United States Patent
Zhang et al.

(10) Patent No.: US 9,005,822 B2
(45) Date of Patent: Apr. 14, 2015

(54) FUNCTIONAL ELECTROLYTE FOR LITHIUM-ION BATTERIES

(71) Applicant: UChicago Argonne, LLC, Chicago, IL (US)

(72) Inventors: Lu Zhang, Lisle, IL (US); Zhengcheng Zhang, Naperville, IL (US); Khalil Amine, Oak Brook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 98 days.

(21) Appl. No.: 13/787,433

(22) Filed: Mar. 6, 2013

(65) Prior Publication Data

US 2014/0255793 A1    Sep. 11, 2014

(51) Int. Cl.
| | |
|---|---|
| H01M 6/16 | (2006.01) |
| C07C 43/205 | (2006.01) |
| H01M 10/052 | (2010.01) |
| H01M 10/0569 | (2010.01) |
| H01M 10/0567 | (2010.01) |

(52) U.S. Cl.
CPC ......... *C07C 43/2055* (2013.01); *H01M 10/052* (2013.01); *H01M 10/0569* (2013.01); *H01M 10/0567* (2013.01)

(58) Field of Classification Search
USPC .......................................... 429/326, 327, 330
See application file for complete search history.

(56) References Cited

U.S. PATENT DOCUMENTS

| | | | |
|---|---|---|---|
| 5,526,599 A | 6/1996 | Roussel | |
| 5,709,968 A | 1/1998 | Shimizu | |
| 5,763,119 A | 6/1998 | Adachi | |
| 5,858,324 A | 1/1999 | Dahn et al. | |
| 5,858,573 A | 1/1999 | Abraham et al. | |
| 5,882,812 A | 3/1999 | Visco et al. | |
| 5,900,385 A | 5/1999 | Dahn et al. | |
| 6,004,698 A | 12/1999 | Richardson et al. | |
| 6,045,952 A | 4/2000 | Kerr et al. | |
| 6,143,268 A | 11/2000 | Dahn et al. | |
| 6,203,944 B1 | 3/2001 | Turner et al. | |
| 6,255,017 B1 | 7/2001 | Turner | |
| 6,387,571 B1 | 5/2002 | Lain et al. | |
| 6,436,578 B2 | 8/2002 | Turner et al. | |
| 6,503,662 B1 | 1/2003 | Hamamoto et al. | |
| 6,664,004 B2 | 12/2003 | Krause et al. | |
| 6,680,145 B2 | 1/2004 | Obrovac et al. | |
| 6,699,336 B2 | 3/2004 | Turner et al. | |

(Continued)

FOREIGN PATENT DOCUMENTS

| | | |
|---|---|---|
| GB | 2 437 902 | 12/2010 |
| JP | 06-338347 | 12/1994 |

(Continued)

OTHER PUBLICATIONS

U.S. Appl. No. 13/457,239, filed Apr. 16, 2012, Wei et al.

(Continued)

*Primary Examiner* — Jane Rhee
(74) *Attorney, Agent, or Firm* — Foley & Lardner LLP

(57) ABSTRACT

Functional electrolyte solvents include compounds having at least one aromatic ring with 2, 3, 4 or 5 substituents, at least one of which is a substituted or unsubstituted methoxy group, at least one of which is a tert-butyl group and at least one of which is a substituted or unsubstituted polyether or poly (ethylene oxide) (PEO) group bonded through oxygen to the aromatic ring, are provided.

18 Claims, 9 Drawing Sheets

(56) References Cited

U.S. PATENT DOCUMENTS

| | | |
|---|---|---|
| 6,964,828 B2 | 11/2005 | Lu et al. |
| 7,078,128 B2 | 7/2006 | Lu et al. |
| 7,211,237 B2 | 5/2007 | Eberman et al. |
| 7,748,497 B2 | 7/2010 | Tolliver et al. |
| 7,851,092 B2 | 12/2010 | Amine et al. |
| 7,968,235 B2 | 6/2011 | Amine et al. |
| 8,283,074 B2 | 10/2012 | Amine et al. |
| 2003/0027048 A1 | 2/2003 | Lu et al. |
| 2003/0211390 A1 | 11/2003 | Dahn et al. |
| 2004/0121234 A1 | 6/2004 | Le |
| 2004/0121239 A1 | 6/2004 | Abe et al. |
| 2004/0179993 A1 | 9/2004 | Dahn et al. |
| 2005/0031957 A1 | 2/2005 | Christensen et al. |
| 2005/0221196 A1 | 10/2005 | Dahn et al. |
| 2006/0046144 A1 | 3/2006 | Obrovac |
| 2006/0199080 A1 | 9/2006 | Amine et al. |
| 2006/0263695 A1 | 11/2006 | Dahn et al. |
| 2009/0286162 A1 | 11/2009 | Lamanna et al. |
| 2010/0040954 A1 | 2/2010 | Amine et al. |
| 2011/0294003 A1* | 12/2011 | Zhang et al. ........ 429/199 |
| 2011/0294017 A1 | 12/2011 | Weng et al. |
| 2011/0294018 A1 | 12/2011 | Zhang et al. |

FOREIGN PATENT DOCUMENTS

| | | |
|---|---|---|
| JP | 07-302614 | 11/1995 |
| JP | 2000-058117 | 2/2000 |
| JP | 2002-260730 | 9/2002 |
| JP | 2004-063112 | 2/2004 |
| JP | 2004-234948 | 8/2004 |
| JP | 2004-349132 | 12/2004 |
| WO | WO-01/29920 | 4/2001 |

OTHER PUBLICATIONS

Chen, J. et al., "Chemical Overcharge and Overdischarge Protection for Lithium-Ion Batteries", Electrochemical and Solid-State Letters, vol. 8, No. 1, pp. A59-A62, 2005.

Chen, Z. et al., "Understanding the Stability of Aromatic Redox Shuttles for Overcharge Protection of Lithium-Ion Cells," Journal of Electrochemical Society, 153, 2006, A2215.

Weng, W., et al., "Improved synthesis of a highly fluorinated boronic ester as dual functional additive for lithium-ion batteries," Power Sources, 2010, pp. 2171-2178.

Zhang, L, et al., "Novel Redox Shuttle Additive for High Voltage Cathode Materials: Tetraethyl2,5-di-tert-Butyl-1,4-Phenylene Diphosphate," Energy & Environmental Science, 2011, pp. 2858-2862.

Zhang, L., "Redox Shuttle Additives for Lithium-Ion Battery," New Developments, Chapter 7, Feb. 24, 2012, 17 pages.

Zhang, L., et al., "Molecular engineering towards safer litium-ion batteries: a highly stable and compatible redox shuttle for overcharge protection," Energy & Environmental Science, 2012,5, pp. 8204-8207.

Zhang, Z, et al., "Understanding the redox shuttle stability of 3,5-di-tert-butyl-1,2-dimethoxybenzene for overcharge protection of lithium-ion batteries," Journal of Power Sources, vol. 195, Issue 15, Aug. 1, 2010, pp. 4957-4962.

\* cited by examiner

FUNCTIONAL ELECTROLYTE FOR LITHIUM-ION BATTERIES

STATEMENT OF GOVERNMENT INTEREST

The United States Government has rights in this invention pursuant to Contract No. DE-AC02-06CH11357 between the U.S. Department of Energy and UChicago Argonne, LLC, representing Argonne National Laboratory.

FIELD

The present technology generally relates to compounds that provide intrinsic overcharge protection in lithium ion batteries, electrical double-layer capacitors and other electrochemical devices.

BACKGROUND

Lithium ion batteries (LIB) were conceived and developed in Japan by Asahi Kasei Co. and first commercialized by Sony Co. in 1991, and soon this novel energy storage technology had drawn tremendous attention from academic and industry communities alike. With many extensive research and engineering efforts conducted, lithium-ion batteries have become the most popular power source for portable electronic devices, such as, but not limited to, cell phones, mp3 players, and laptop computers. In addition, applications for use in the hybrid vehicle (HEV) and plug-in hybrid electric vehicle (PHEV) are being actively investigated. However, the improvements in battery performance must also be mindful of safety issues. When more energy or capacity is stored in the cell, the system becomes more thermodynamically unstable. For secondary lithium-ion batteries, dangerous results could be triggered under certain situations such as shortage, elevated temperature and overcharge.

Overcharge is a battery condition where electrical flow is forced through a cell after the capacity of the cell has been already been reached. Overcharge is one of the more common factors that could lead to serious safety issues in lithium-ion batteries. The phenomenon is most likely to occur during the charging of a battery pack. Due to the manufacturing processes, there will always be a weakest cell with the lowest capacity in one battery pack. During charging, the weak cell will always reach its full capacity before the other cells and without triggering the voltage monitor of the charger because the voltage of the full pack is still within the normal range. But the weak cell is none-the-less in a state of overcharge. As a result, extra electricity will build up on the surface of the electrodes instead of being stored, thereby dramatically increasing the potential of the cathode. As the charging is continued, the potential will go beyond the electrochemical window of the electrolyte and cause various reactions of the electrolyte. For example, oxidation of the electrolyte may occur and thereby trigger other reactions. The cell may end up in a thermal runaway, or even result in an explosion.

SUMMARY

In one aspect, a functional electrolyte solvent is provided, which includes a compound having the formula I,

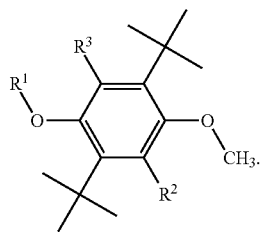

In the compound have the formula I, $R^1$ is

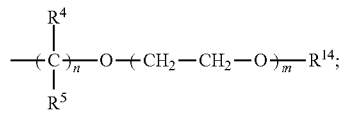

$R^2$ and $R^3$ are each independently H, F, Cl, Br, I, alkyl, or a polyether group; $R^4$ and $R^5$ are each independently H, F, Cl, Br, I, CN, $NO_2$, alkyl, haloalkyl, phosphate, polyether groups; $R^{14}$ is H, alkyl or haloalkyl; m is an integer from 1 to 20, inclusive; and n is an integer from 1 to 16, inclusive.

In some embodiments, $R^1$ is selected from

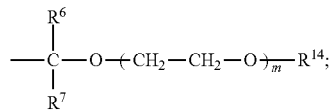

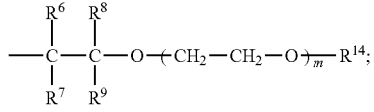

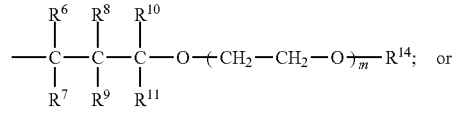

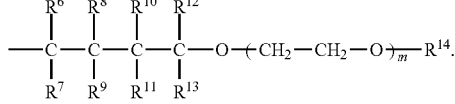

In formulas II-1 through II-4, each of $R^6$-$R^{13}$ is independently H, F, Cl, Br, I, CN, $NO_2$, alkyl, haloalkyl, phosphate, polyether groups; $R^{14}$ is H, alkyl or haloalkyl group; m is an integer from 1 to 20, inclusive; and n is an integer from 1 to 16, inclusive.

In some embodiments, the compound of formula I has the structure

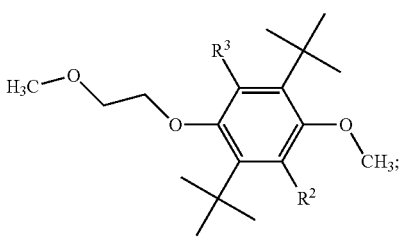

where $R^2$ and $R^3$ are each independently H, F, Cl, Br, I, alkyl, or a polyether group. In other embodiments, the compound of formula I has the structure

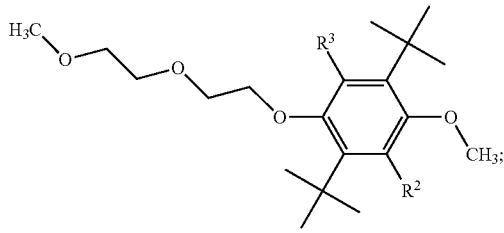

where $R^2$ and $R^3$ are each independently H, F, Cl, Br, I, alkyl, or a polyether group.

In one aspect, the functional electrolyte solvent is 1-(2-methoxyethoxy)methoxy-4-methoxy-2,5-di-tert-butyl-benzene, 1-[2-(2-methoxyethoxy)ethoxy]-4-methoxy-2,5-di-tert-butyl-benzene, or a mixture thereof.

In another aspect, an electrolyte is provided, which includes the functional electrolyte solvent and an alkali metal salt. In some embodiments, the functional electrolyte solvent is a redox active material and has a redox potential of 3 to 5 V versus Li/Li$^+$. In some embodiments, the concentration of the functional electrolyte solvent in the electrolyte is from 0.0005 wt % and 60 wt %. In some embodiments, the alkali metal salt is a lithium salt. In some embodiments, the alkali metal salt is Li[(C$_2$O$_4$)$_2$B], Li(C$_2$O$_4$)BF$_2$, LiClO$_4$, LiBF$_4$, LiAsF$_6$, LiPF$_6$, LiCF$_3$SO$_3$, Li(CF$_3$SO2)2N, Li(CF$_3$SO$_2$)$_3$C, LiN(SO$_2$C$_2$F$_5$)$_2$, lithium alkyl fluorophosphates, or a mixture of any two or more thereof.

In one aspect, the electrolyte further includes a polar aprotic solvent. In some embodiments, the polar aprotic solvent is selected from ethylene carbonate, propylene carbonate, dimethyl carbonate, diethyl carbonate, ethyl methyl carbonate, dimethyl ether, gamma butyrolactone, or a mixture of any two or more thereof.

In some embodiments, the alkali metal salt is other than Li[(C$_2$O$_4$)$_2$B], Li(C$_2$O$_4$)BF$_2$, and the electrolyte further comprises about 0.001 wt % to about 8 wt % of an electrode stabilizing additive that is Li[(C$_2$O$_4$)$_2$B], Li(C$_2$O$_4$)BF$_2$, or a mixture thereof. In some embodiments the electrolyte further includes an electrode stabilizing additive that is a substituted or unsubstituted spirocyclic hydrocarbon containing at least one oxygen atom and at least one alkenyl or alkynyl group.

In yet another aspect, an electrochemical device is provided, which includes a cathode, an anode and an electrolyte which includes a functional electrolyte solvent. In some embodiment, the electrochemical device is a lithium secondary battery; the cathode is a lithium metal oxide cathode; the anode is a carbon or lithium metal anode; and the anode and cathode are separated from each other by a porous separator.

BRIEF DESCRIPTION OF THE DRAWINGS

The foregoing and other objects, aspects, features and advantages of the disclosure will become more apparent and better understood by referring to the following description taken in conjunction with the accompanying drawings, in which.

DETAILED DESCRIPTION

Figure 1:
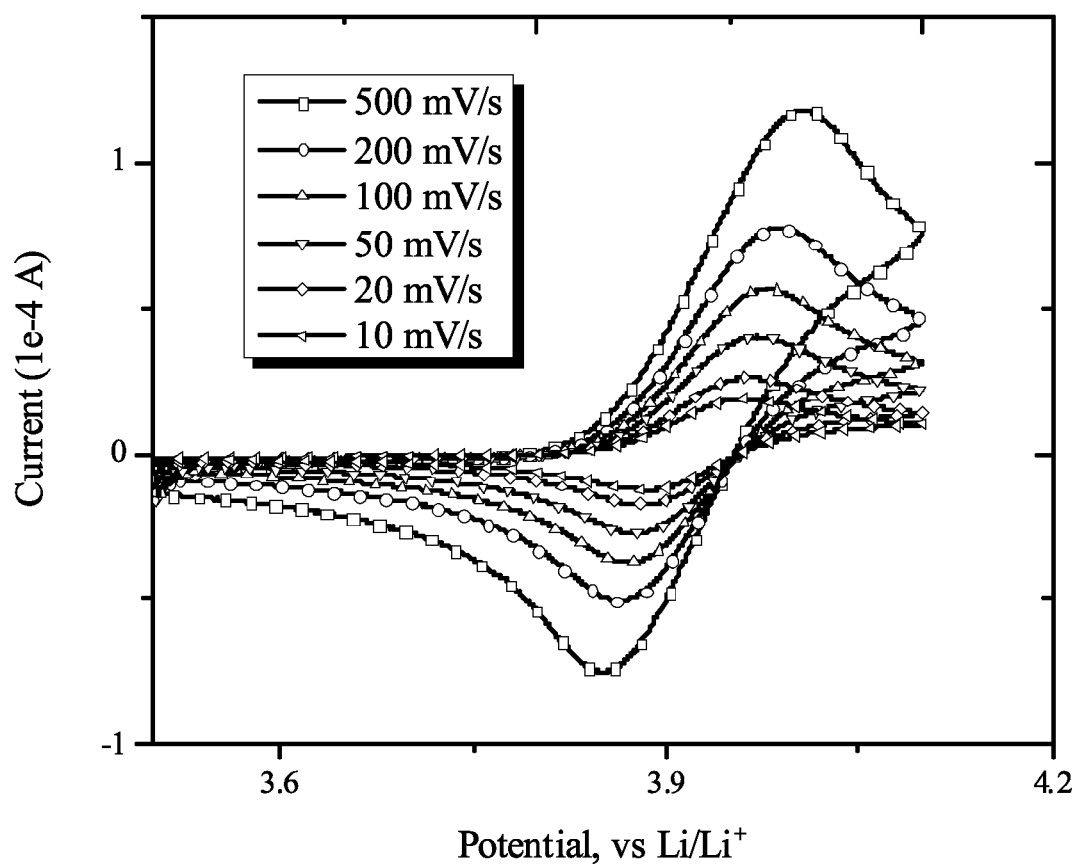
FIG. 1 illustrates a cyclic voltammogram of an electrolyte that includes 0.01 M 1-methoxy-4-(2-methoxyethoxy)-2,5-di-tert-butyl-benzene in 1.2M LiPF$_6$ in EC/EMC (3:7 by weight) at various scan rates using a Pt/Li/Li three-electrode system (Pt working Electrode, Li counter electrode and Li reference electrode), according to Example 1.

In the following detailed description, reference is made to the accompanying drawings, which form a part hereof. In the drawings, similar symbols typically identify similar components, unless context dictates otherwise. The illustrative embodiments described in the detailed description, drawings and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined and designed in a wide variety of different configurations, all of which are explicitly contemplated and made part of this disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term.

The use of the terms "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen or carbon atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Unless expressly indicated otherwise, alkyl groups may be substituted, or unsubstituted, and if no designation is used, it is assumed that the alkyl group may be either substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein, the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6 or 7. Unless expressly indicated otherwise, cycloalkyl groups may be substituted or unsubstituted, and if no designation is used, it is assumed that the cycloalkyl group may be either substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1-12 carbons or, typically, from 1-8 carbon atoms. Unless expressly indicated otherwise, alkenyl groups may be substituted or unsubstituted, and if no designation is used, it is assumed that the alkenyl group may be either substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl" groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6-12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be either substituted and unsubstituted aryl groups and if no designation is used, it is assumed that the aryl group may be either substituted or unsubstituted. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As defined herein, an "aromatic" group include those groups identified as aryl groups, but where aryl group is used to define substituent groups on a primary structure, the aromatic ring is the primary structure. Thus, aromatic rings include monocyclic, bicyclic and polycyclic ring systems. Aromatic rings include, but are not limited to, benzene rings, azulene rings, biphenylene rings, indacene rings, fluorine rings, pyrene rings, phenanthrene rings, triphenylene rings, naphthacene rings, chrysene rings, anthracene rings, heptalene rings, indene rings, indane rings, pentalene rings, and naphthylene rings. In some embodiments, aromatic rings contain 6-14 carbons, and in others from 6-12 or even 6-10 carbon atoms in the ring portions. Aromatic rings may be either substituted or unsubstituted aryl groups and if no designation is used, it is assumed that the aromatic ring may be either substituted or unsubstituted. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, "aralkyl" groups are alkyl groups as defined above in which a hydrogen or carbon bond of an alkyl group is replaced with a bond to an aryl group as defined above. In some embodiments, aralkyl groups contain 7-20 carbon atoms, 7-14 carbon atoms or 7-10 carbon atoms. Unless expressly indicated otherwise, aralkyl groups may be substituted or unsubstituted, and if no designation is used, it is assumed that the aralkyl group may be either substituted or unsubstituted.

As used herein, "heterocyclyl" groups includes non-aromatic ring compounds containing 3 or more ring members, of which one or more is a heteroatom such as, but not limited to, N, O, and S. In some embodiments, heterocyclyl groups include 3-20 ring members, whereas other such groups have 3-6, 3-10, 3-12, or 3-15 ring members. Heterocyclyl groups encompass unsaturated, partially saturated and saturated ring systems, such as, for example, imidazolyl, imidazolinyl and imidazolidinyl groups. Unless expressly indicated otherwise, heterocyclyl groups may be substituted or unsubstituted, and if no designation is used, it is assumed that the heterocyclyl group may be either substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl(pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl(azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

As used herein, "heteroaryl" groups are aromatic ring compounds containing 5 or more ring members, of which one or more is a heteroatom such as, but not limited to, N, O, and S. Unless expressly indicated otherwise, heteroaryl groups may be substituted or unsubstituted, and if no designation is used, it is assumed that the heteroaryl group may be either substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl(pyrrolopyridyl), indazolyl, benzimidazolyl, imidazopyridyl(azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

As used herein, "alkoxy" groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tert-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Representative substituted alkoxy groups may be substituted one or more times with substituents such as those listed above.

In one aspect, a functional electrolyte solvent is provided. In some embodiments, the functional electrolyte solvents are compounds having at least one aromatic ring with 2, 3, 4 or 5 substituents, at least one of which is a substituted or unsubstituted methoxy group, at least one of which is a tert-butyl group and at least one of which is a substituted or unsubstituted polyether or poly(ethylene oxide) (PEO) group bonded through oxygen to the aromatic ring. Examples of such aromatic rings include benzene, naphthalene, anthracene, biphenyl, and the like. The tertiary carbon organic group may have the formula —CR$_3$ where each R group independently has up to 10, up to 6, up to 4, up to 2, or 1 carbon atom. Exemplary tertiary carbon organic groups may, for example, have up to 12, up to 10, up to 8, up to 6, 5 or 4 carbon atoms. Some shuttles in this subclass may contain two, or at least two, tertiary carbon organic groups which may be the same or different. If located on the same aromatic ring (e.g., a benzene ring), the tertiary carbon organic groups may, for example, be oriented ortho, meta or para to one another. In some embodiments, the tertiary carbon organic group is a tertiary butyl group. Other substituents may be present on the shuttle aromatic ring or rings or on the tertiary carbon organic group(s), so long as such substituents do not unduly interfere with factors such as the shuttle's charge-carrying capability, oxidation potential or stability. Some exemplary embodiments do not contain readily-polymerizable ring substituents (e.g., allyl groups) or halogen atoms. The functional electrolyte solvent may also be in the form of a salt.

In some embodiments, the functional electrolyte solvents include a 1,4-di-tertiary butyl compound having a 2-methoxy group and a 5-alkoxy group, where the alkoxy group is other than methoxy. Such compounds are non-symmetrical and provide enhanced solubility and solubilizing properties.

In some embodiments, the functional electrolyte solvent includes a compound having the formula I:

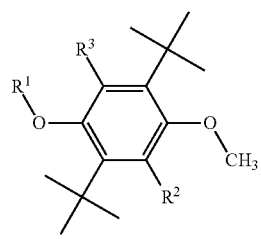

I

In formula I, R$^2$ is H, F, Cl, Br, I, alkyl, or a polyether, R$^3$ is H, F, Cl, Br, I, alkyl, or a polyether, and R$^1$ may be a group of formula II, which is:

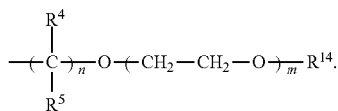

In formula II, $R^4$ is H, F, Cl, Br, I, CN, $NO_2$, alkyl, haloalkyl, phosphate, or a polyether; $R^5$ is H, F, Cl, Br, I, CN, $NO_2$, alkyl, haloalkyl, phosphate, or a polyether; $R^{14}$ is H, alkyl or haloalkyl; m is an integer from 1 to 20, inclusive; and n is an integer from 1 to 16, inclusive. In some embodiments, $R^2$ is H, F, Cl, Br, I, $C_1$-$C_8$ alkyl, or a polyether, $R^3$ is H, F, Cl, Br, I, $C_1$-$C_8$ alkyl, or a polyether; $R^4$ is H, F, Cl, Br, I, CN, $NO_2$, $C_1$-$C_8$ alkyl, $C_1$-$C_8$ haloalkyl, phosphate, or a polyether; $R^5$ is H, F, Cl, Br, I, CN, $NO_2$, $C_1$-$C_8$ alkyl, $C_1$-$C_8$ haloalkyl, phosphate, or a polyether; $R^{14}$ is H, $C_1$-$C_8$ alkyl or $C_1$-$C_8$ haloalkyl; m is an integer from 1 to 20, inclusive; and n is an integer from 1 to 16, inclusive. In some embodiments, $R^2$ is H, F, Cl, methyl, or ethyl, $R^3$ is H, F, Cl, methyl, or ethyl; $R^4$ is H, F, Cl, methyl, ethyl, or a polyether; $R^5$ is H, F, Cl, methyl, ethyl, or a polyether; $R^{14}$ is H, methyl, or ethyl; m is an integer from 1 to 20, inclusive; and n is an integer from 1 to 16, inclusive.

In some embodiments, $R^1$ is a group of formulas II-1 through II-5. Formulas II-1 through II-4 include:

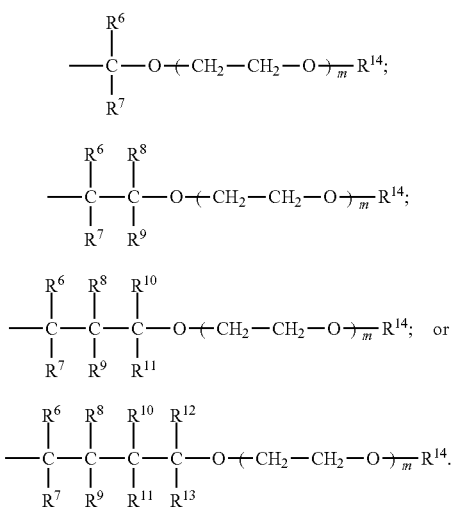

In formulas II-1 through II-4, each of $R^6$-$R^{13}$ is independently H, F, Cl, Br, I, CN, $NO_2$, alkyl, a haloalkyl, a phosphate, or a polyether group; $R^{14}$ is H, alkyl or a haloalkyl group; m is an integer from 1 to 20, inclusive; and n is an integer from 1 to 16, inclusive. In some embodiments, each of $R^6$-$R^{13}$ is independently H, F, Cl, Br, I, $C_1$-$C_8$ alkyl, a $C_1$-$C_8$ haloalkyl, or a polyether group; $R^{14}$ is H, $C_1$-$C_8$ alkyl or a $C_1$-$C_8$ haloalkyl group; m is an integer from 1 to 20, inclusive; and n is an integer from 1 to 16, inclusive. In some embodiments, each of $R^6$-$R^{13}$ is independently H, F, Cl, Br, I, $C_1$-$C_4$ alkyl, a $C_1$-$C_4$ haloalkyl, or a polyether group; $R^{14}$ is H, $C_1$-$C_4$ alkyl or a $C_1$-$C_4$ haloalkyl group; m is 1, 2, 3, 4, 5, 6, 7, 8 an integer from 1 to 20, inclusive; and n is an integer from 1 to 16, inclusive. In some embodiments, each of $R^6$-$R^{13}$ is independently H, F, Cl, methyl or ethyl; $R^{14}$ is H, methyl, or ethyl; m is 1, 2, 3, 4, 5, 6, 7, or 8; and n is 1, 2, 3, 4, 5, 6, 7, or 8. In one embodiment, $R^1$ is a group of formula II-2, $R^2$, $R^3$, $R^6$, $R^7$, $R^8$, and $R^9$ are H; $R^{14}$ is methyl, or ethyl; and m is 1, 2, 3, 4, 5, 6, 7, or 8.

In some embodiments, the compound of formula I has the structure

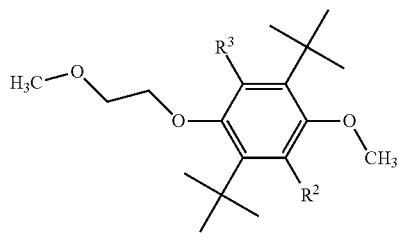

wherein $R^2$ is H, F, Cl, Br, I, alkyl, or a polyether group, and $R^3$ is H, F, Cl, Br, I, alkyl, or a polyether group. In some embodiments, $R^2$ is H, F, Cl, methyl, ethyl, or a polyether group, and $R^3$ is H, F, Cl, methyl, ethyl, or a polyether group. In some embodiments, $R^2$ is H, and $R^3$ is H.

In some embodiments, wherein the compound of formula I has the structure

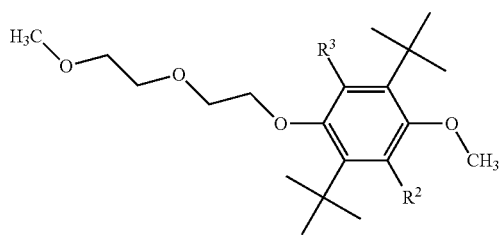

wherein $R^2$ is H, F, Cl, Br, I, alkyl, or a polyether group, and $R^3$ is H, F, Cl, Br, I, alkyl, or a polyether group. In some embodiments, $R^2$ is H, F, Cl, methyl, ethyl, or a polyether group, and $R^3$ is H, F, Cl, methyl, ethyl, or a polyether group. In some embodiments, $R^2$ is H, and $R^3$ is H.

In some embodiments, the factional electrolyte solvent is 1-methoxy-4-(2-methoxyethoxy)-2,5-di-tert-butyl-benzene, 1-methoxy-4-[2-(2-methoxyethoxy)ethoxy]-2,5-di-tert-butyl-benzene, or a mixture thereof. In other embodiments, the functional electrolyte solvent is 1-methoxy-4-[2-[2-(2-ethoxyethoxy)ethoxy]ethoxy]-2,5-di-tert-butyl-benzene, 1-methoxy-4-[2-[2-[2-(2-methoxyethoxy)ethoxy]ethoxy]ethoxy]-2,5-di-tert-butyl-benzene, 1-methoxy-4-[2-[2-[2-[2-(2-methoxyethoxy)ethoxy]ethoxy]ethoxy]ethoxy]-2,5-di-tert-butyl-benzene, 1-methoxy-4-[2-[2-[2-[2-[2-(2-methoxyethoxy)ethoxy]ethoxy]ethoxy]ethoxy]ethoxy]-2,5-di-tert-butyl-benzene.

The functional electrolyte solvents are typically non-aqueous. As used herein, non-aqueous means that the water content of the electrolyte or solvent is minimal, or only an adventitious amount of water is present. In some embodiments, less than 20 parts per million (ppm) of water is present. In other embodiments, less than 15 ppm of water is present. In various other embodiments, less than 10 ppm, or even less than 5 ppm, of water is present. Substantially non-aqueous electrolyte solvents also include embodiments where no water is present.

In one embodiment, the functional electrolyte solvents are redox active materials and have a redox potential of about 3.5 V to about 5.0 V. In some embodiments, the functional electrolytes have a redox potential of about 3.6 V to about 4.6 V.

In some embodiments, the functional electrolyte solvents are liquid redox active materials or redox shuttles that may not only be used as electrolyte solvents or co-solvents, but they may also be configured to provide overcharge protection to the devices they are included in, e.g., lithium-ion batteries.

In another aspect, an electrolyte is provided, which includes a functional electrolyte solvent and an alkali metal salt.

The functional electrolyte solvents are present in the electrolyte in concentrations suitable the concentration of the functional electrolyte solvent in the electrolyte is from 0.0005 wt % and 60 wt %.

In some embodiments, the electrolyte further includes a polar aprotic solvent. Suitable polar aprotic solvents are known in the art and include, but are not limited to ethylene carbonate, propylene carbonate, dimethyl carbonate, diethyl carbonate, ethyl methyl carbonate, dimethyl ether, gamma butyrolactone, or a mixture of any two or more thereof.

Any of the functional electrolyte solvents described above may be used in an electrochemical device having an anode (negative electrode), a cathode (positive electrode), and the electrolyte. Examples of such electrochemical devices include all kinds of primary batteries, secondary batteries, fuel cells, biofuel cells, flywheels, solar cells, and capacitors such as supercapacitor devices. In some embodiments, the electrochemical cell is a primary cell. In some embodiments, the primary cell that is a lithium/MnO2 battery or Li/poly (carbon monofluoride) battery. In some embodiments, the electrochemical device is a lithium secondary battery. In some embodiments, the secondary battery is a lithium battery, a lithium-ion battery, a lithium-sulfur battery, a lithium-air battery, a sodium ion battery, or a magnesium battery. In one embodiment, the electrochemical device is a lithium-ion battery.

A variety of salts, including alkali metal salts, may be employed in the electrolytes and electrochemical devices, and will be known to those of skill in the art. In some embodiments, e.g., in lithium-ion batteries, the alkali metal salt is a lithium salt. Illustrative salts are $LiPF_6$, $LiClO_4$, $(C_4BO_8Li)$, $(C_2BO_4F_2Li)$, $LiPF_4C_2O_4$, $Li(CF_3SO_2)_2N$, $LiC(SO_2CF_3)_3$, $(Li(C_2F_5SO_2)_2N)$, $LiCF_3SO_3$, $Li_2B_{12}X_{12-n}H_n$, $Li_2B_{10}X_{10-n}H_{n'}$, where X is a halogen, n is an integer from 0 to 12, and n' is an integer from 0 to 10, $LiAlF_4$, $LiBF_4$, $Li(FSO_2)_2N$, $Li_2SO_4$, $Na_2SO_4$, $NaPF_6$, $NaClO_4$, $LiAlO_2$, LiSCN, LiBr, LiI, $LiAsF_6$, $LiB(Ph)_4$, $LiSO_3CH_3$, $Li_2S_{x''}$, $Li_2Se_{x''}$, $(LiS_{x''}R)_y$, or $(LiSe_{x''}R)_y$; wherein x" is an integer from 1 to 20, y is an integer from 1 to 3 and R is H, alkyl, alkenyl, aryl, ether, F, $CF_3$, $COCF_3$, $SO_2CF_3$, or $SO_2F$.

In some embodiments, the alkali metal salt is other than $Li[(C_2O_4)_2B]$, $Li(C_2O_4)BF_2$, and the electrolyte further comprises about 0.001 wt % to about 8 wt % of an electrode stabilizing additive that is $Li[(C_2O_4)_2B]$, $Li(C_2O_4)BF_2$, or a mixture thereof.

A variety of negative electrodes or anodes may be employed in the electrochemical devices such as lithium-ion batteries. Representative negative electrodes include $Li_{4/3}Ti_{5/3}O_4$; the lithium alloy compositions; graphitic carbons, such as, those having a spacing between (002) crystallographic planes, d 002, of 3.45 Å>d 002>3.354 Å and existing in forms such as powders, flakes, fibers Å or spheres (e.g., mesocarbon microbeads); and other materials that will be familiar to those skilled in the art; and combinations thereof.

A variety of current collectors may be employed in the electrochemical devices such as lithium-ion batteries. Often, the negative and positive electrodes will be carried on the current collector, with the current collector serving as a support. The current collector may also be an adjacent material, e.g., a shell of a lithium-ion button cell. A variety of arrangements will work, so long as the negative and positive electrodes make suitable electrical contact with their associated current collector.

Some guidelines may aid in selecting the negative electrode current collector. To prevent lithium capture during recharging, the negative electrode current collector has a lithium alloying potential below the negative electrode's minimum normal operating potential. Thus, the negative electrode current collector selection will be guided in part by the negative electrode selection. To discourage or prevent current collector dissolution during overdischarging, it may be helpful to employ a negative electrode current collector having a dissolution potential above the shuttle reduction potential. Thus, the negative electrode current collector selection may also be guided in part by the shuttle selection.

Representative negative electrode current collectors include aluminum, copper, stainless steels (e.g., 300 series and 400 series stainless steels), titanium, tantalum, niobium, INCONEL™ nickel chromium alloys (commercially available from International Nickel Co.), combinations thereof and other materials that will be familiar to those skilled in the art. Aluminum has a lithium alloying potential of about 0.3 V vs Li. Most of the other listed materials are believed to have lithium alloying potentials below 0 V. Copper is believed to have a dissolution potential below about 4.0 V. Most of the other listed materials are believed to have dissolution potentials above 4.0 V. The current collector may be monolithic throughout, or may have a surface or exposed layer whose composition is different from the composition of the underlying current collector material. Aluminum appears to offer especially good performance.

When the negative electrode has a larger irreversible first cycle capacity loss than that of the positive electrode, the positive electrode will normally remain at an elevated potential during overdischarge. Its current collector will be held near the same elevated potential and will not be susceptible to lithium capture during recharging or dissolution during overdischarging. Accordingly there are fewer constraints on selection of the positive electrode current collector. Representative positive electrode current collectors include aluminum, stainless steels (e.g., 300 series and 400 series stainless steels), titanium, tantalum, niobium, INCONEL alloys, combinations thereof and other materials that will be familiar to those skilled in the art.

A variety of positive electrodes or cathodes may be employed in the electrochemical devices such as lithium-ion batteries. Illustrative cathode materials include, but are not limited to, spinel, olivine, carbon-coated olivine, $LiMnPO_4$, $LiMn_2O_4$, $LiCoPO_4$, $LiCoO_2$, $LiFePO_4$, $LiCoO_2$, $LiNiO_2$, $LiNi_{1-x}Co_yMet'_zO_2$, $LiMn_{0.5}Ni_{0.5}O_2$, $LiMn_{0.3}Co_{0.3}Ni_{0.3}O_2$, $LiMn_2O_4$, $LiFeO_2$, $LiMet_{0.5}Mn_{1.5}O_4$, $Li_{1+x}Ni_\alpha Mn_\beta Co_\gamma Met'_\delta O_{2-z}F_z$, $A_nB_2(XO_4)_3$ (Nasicon), vanadium oxide, or mixtures of any two or more thereof, wherein Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, or Zn; B is Ti, V, Cr, Fe, or Zr; X is P, S, Si, W, or Mo; and $0 \leq x \leq 0.3$, $0 \leq y \leq 0.5$, $0 \leq z \leq 0.5$, $0 \leq x' \leq 0.4$, $0 \leq \alpha \leq 1$, $0 \leq \beta \leq 1$, $0 \leq \gamma \leq 1$, $0 \leq \delta \leq 0.4$, $0 \leq z' \leq 0.4$, and $0 \leq n' \leq 3$. Other cathode materials include lithium transition metal oxides as disclosed in U.S. Pat. Nos. 5,858,324; 5,900,385; 6,143,268; 6,964,828; 7,078,128; 7,211,237; and 6,680,145; and in U.S. Patent Application Publication Nos. 2003/0027048; 2004/0121234; 2004/0179993; and 2006/045144; and in combinations of any two or more such materials.

The negative or positive electrode may contain additives such as will be familiar to those skilled in the art, e.g., carbon black for negative electrodes and carbon black, flake graphite and the like for positive electrodes.

The negative and positive electrode capacities may optionally be selected to provide an excess negative electrode capacity. This enables the factional electrolyte solvents operating as redox active materials or redox shuttle materials as to provide overcharge protection. About 10 to about 20% excess negative electrode capacity is recommended. Lesser or greater excess negative electrode capacities may be employed if desired.

A variety of charge carrying media may be employed in the electrolyte. Exemplary media are liquids or gels capable of solubilizing sufficient quantities of the alkali metal salt and the functional electrolyte solvent so that a suitable quantity of charge can be transported from the positive electrode to negative electrode. Exemplary charge carrying media can be used over a wide temperature range, e.g., from about −30° C. to about 70° C. without freezing or boiling, and are stable in the electrochemical window within which the cell electrodes and shuttle operate. Representative charge carrying media include ethylene carbonate, propylene carbonate, dimethyl carbonate, diethyl carbonate, ethyl-methyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), combinations thereof and other materials that will be familiar to those skilled in the art.

In addition to the functional electrolyte solvents which operate as redox active materials or redox shuttle materials, a variety of additional redox chemical shuttles may be employed in electrochemical devices. The shuttle, if present, will have an electrochemical potential above (e.g., slightly above) the positive electrode's maximum normal operating potential. Thus, the shuttle selection may be guided in part by the positive electrode selection. As a general numeric guide, the shuttle may, for example, have a redox potential about 0.3 to 0.6 V above the positive electrode's maximum normal operating potential, e.g., about 3.7 to about 4.7 V vs. Li/Li$^+$, about 3.7 to about 4.4 V vs. Li/Li$^+$, about 3.7 to about 4.2 V vs. Li/Li$^+$, or about 3.7 to about 4.0 V vs. Li/Li$^+$. For example, LiFePO$_4$ positive electrodes have a recharge plateau around 3.45 V vs. Li/Li$^+$, and exemplary shuttles for use with such electrodes may have a redox potential from about 3.75 to about 4.05 V vs. Li/Li$^+$. Similarly, LiMnPO$_4$ and LiMn$_2$O$_4$ electrodes have a recharge plateau around 4.1 V vs. Li/Li$^+$, and exemplary shuttles for use with such electrodes may have a redox potential from about 4.4 to about 4.7 V vs. Li/Li$^+$.

Illustrative additional redox shuttles include, but are not limited to, anisole, substituted anisoles (or methoxybenzenes) such as 2-methylanisole, 2-ethylanisole, 2-tert-butylanisole, 3-tert-butyl-anisole, 4-tert-butyl-anisole, 2-bromoanisole, 4-bromoanisole, 2,4,6-tribromoanisole, 3,5 dichloroanisole, 2,4,6-trichloroanisole, 4-bromo-2-fluoroanisole, 1-cyclopropyl-2-methoxybenzene, 1-nitro-3-tert-butyl-2-methoxybenzene, 1-cyano-3-tert-butyl-2-methoxybenzene, 1,4-di-tert-butyl-2-methoxybenzene, 5-tert-butyl-1,3-dinitro-2-methoxybenzene, 1-(benzyloxy)-4-bromo-2-methoxybenzene, 1,3,5-tri-tert-butyl-2-methoxybenzene, 1-[(2-ethylhexyl)oxy]-4-methoxybenzene, 1-hexadecyloxy-4-methoxybenzene, 1-((((ethoxycarbonyl)oxy)imino)methyl)-4-methoxybenzene and 2-tert-pentyl-anisole; alkoxy-substituted phthalates such as 4-methoxyphthalate; alkoxy-substituted catechols such as 3-methoxycatechol; substituted di-alkoxybenzenes such as 2-methyl-1,4-dimethoxybenzene, 2,3-dimethyl-1,4-dimethoxybenzene, 2,5-dimethyl-1,4-dimethoxybenzene, 2,6-dimethyl-1,4-dimethoxybenzene, 2,3,6-trimethyl-1,2-dimethoxybenzene, 2,3,5,6-tetramethyl-1,4-dimethoxybenzene, 4-methyl-1,2-dimethoxybenzene, 2,3,5,6-tetramethyl-1,4-dimethoxybenzene, 2-ethyl-1,4-dimethoxybenzene, 2,3-diethyl-1,4-dimethoxybenzene, 2,5-diethyl-1,4-dimethoxybenzene, 2,6-diethyl-1,4-dimethoxybenzene, 2,3,6-triethyl-1,2-dimethoxybenzene, 2,3,5,6-tetraethyl-1,4-dimethoxybenzene, 4-ethyl-1,2-dimethoxybenzene, 2,5-diisopropyl-1,4-dimethoxybenzene, 2-tert-butyl-1,4-dimethoxybenzene, 2,3-di-tert-butyl-1,4-dimethoxybenzene, 2,5-di-tert-butyl-1,4-dimethoxybenzene, 2,5-di-tert-pentyl-1,4-dimethoxybenzene, 2,5-di-tert-butyl-3,6-dinitro-1,4-dimethoxybenzene, 2,5-di-tert-butyl-3,6-di-cyano-1,4-dimethoxybenzene, 2,5-di-tert-butyl-1,4-dimethoxybenzene, 2,5-di-tert-butyl-1,4-diethoxybenzene, 2,5-dicyclohexyl-1,4-dimethoxybenzene, 4-tert-butyl-1,2-dimethoxybenzene, 4,5-di-tert-butyl-1,2-dimethoxybenzene, 4,5-di-tert-pentyl-1,2-dimethoxybenzene and 4,5-di-tert-butyl-1,2-diethoxybenzene; substituted alkoxynaphthalenes such as 4,8-di-tert-butyl-1,5-dimethoxynaphthalene; polycyclic compounds such as 1-(3-(2,4-cyclopentadien-1-ylidene)-1-butenyl)-4-methoxybenzene, 9,10-dimethoxy-1,4:5,8-dimethano-1,2,3,4,5,6,7,8-octahydroanthracene and 9,10-dimethoxy-1,4:5,8-diethano-1,2,3,4, 5,6,7,8-octahydroanthracene; and salts such as 3-amino-n-dodecyl-4-methoxybenzene-sulfonamide and 3-methoxybenzyl bromide.

In some embodiments, the non-aqueous electrolytes which include the functional electrolyte solvent may also include an electrode stabilizing additive to protect the electrodes from degradation. See, e.g., co-pending U.S. Pat. Nos. 7,968,235, and 7,748,497. Thus, electrolytes can include an electrode stabilizing additive that can be reduced or polymerized on the surface of a negative electrode to form a passivation film on the surface of the negative electrode. Likewise, electrolytes can include an electrode stabilizing additive that can be oxidized or polymerized on the surface of the positive electrode to form a passivation film on the surface of the positive electrode. In some embodiments, electrolytes further include mixtures of the two types of electrode stabilizing additives. The additives are typically present at a concentration of about 0.001 to 8 wt %.

In some embodiments, an electrode stabilizing additive is a substituted or unsubstituted linear, branched or cyclic hydrocarbon comprising at least one oxygen atom and at least one aryl, alkenyl or alkynyl group. The passivating film formed from such electrode stabilizing additives may also be formed from a substituted aryl compound or a substituted or unsubstituted heteroaryl compound where the additive comprises at least one oxygen atom. Alternatively, a combination of two additives may be used. In some such embodiments, one additive is selective for forming a passivating film on the cathode to prevent leaching of metal ions and the other additive can be selective for passivating the anode surface to prevent or lessen the reduction of metal ions at the anode.

Representative electrode stabilizing additives include 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone, or a mixture of any two or more thereof. In some embodiments, the electrode stabilizing additive may be a cyclotriphosphazene that is substituted with F, alkyloxy, alkenyloxy, aryloxy, methoxy, allyloxy groups, or combinations thereof. For example, the additive may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)-cyclotriphosphazene, (diaryloxy)(trifluoro)(methoxy)cyclotriphosphazene compounds, or a mixture of two or more such compounds. In some embodiments, the electrode stabilizing additive is vinyl ethylene carbonate, vinyl carbonate, or 1,2-diphenyl ether, or a mixture of any two or more such compounds.

Other representative electrode stabilizing additives may include compounds with phenyl, naphthyl, anthracenyl, pyrrolyl, oxazolyl, furanyl, indolyl, carbazolyl, imidazolyl, or thiophenyl groups. For example, electrode stabilizing additives may be aryloxpyrrole, aryloxy ethylene sulfate, aryloxy pyrazine, aryloxy-carbazole trivinylphosphate, aryloxyethyl-2-furoate, aryloxy-o-terphenyl, aryloxy-pyridazine, butyl-aryloxy-ether, divinyl diphenyl ether, (tetrahydro-furan-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyltetrahydrofuran, 2,4-divinyl isooxazole, 3,4 divinyl-1-methylpyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cyclolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methylpyrrole, naphthalene, or a mixture of any two or more such compounds.

In other embodiments, electrode stabilizing additives include, but are not limited to, substituted or unsubstituted spirocyclic hydrocarbons containing at least one oxygen atom and at least one alkenyl or alkynyl group. For example, such stabilizing additives include those having Formula III:

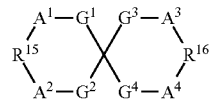

III wherein $A^1$, $A^2$, $A^3$, and $A^4$ are independently O or $CR^{12}R^{13}$; provided that $A^1$ is not O when $G^1$ is O, $A^2$ is not O when $G^2$ is O, $A^3$ is not O when $G^3$ is O, and $A^4$ is not O when $G^4$ is O; $G^1$, $G^2$, $G^3$, and $G^4$ are independently O or $CR^{12}R^{13}$; provided that $G^1$ is not O when $A^1$ is O, $G^2$ is not O when $A^2$ is O, $G^3$ is not O when $A^3$ is O, and $G^4$ is not O when $A^4$ is O; $R^{15}$ and $R^{16}$ are independently a substituted or unsubstituted divalent alkenyl or alkynyl group.

Representative examples of Formula III include, but are not limited to, 3,9 divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9 diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9 dimethylene-1,5,7,11-tetraoxaspiro[5.5]undecane, 3,9 diethylidene-1,5,7,11-tetraoxaspiro[5.5]undecane, or a mixture of any two or more such compounds. Furthermore, mixtures of any two or more electrode stabilizing additives may also be used in the electrolytes of the present technology.

In some embodiments, the electrode stabilizing additive is an anion receptor. In some embodiments, the anion receptor is a Lewis acid. In other embodiments, the anion receptor is a borane, a boronate, a borate, a borole, or a mixture of any two or more such compounds.

In some embodiments, the anion receptor is a compound of the Formula IV:

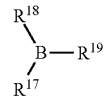

IV where, each $R^{17}$, $R^{18}$, and $R^{19}$ are independently halogen, alkyl, aryl, halogen-substituted alkyl, halogen-substituted aryl, or $OR^{17}$; or any two of $R^{17}$, $R^{18}$, and $R^{19}$, together with the atoms to which they are attached, form a heterocyclic ring having 5-9 members, and $R^{17}$ is at each occurrence independently alkyl, aryl, halogen-substituted alkyl, or halogen-substituted aryl.

In some embodiments, the anion receptors include, but are not limited to, tri(propyl)borate, tris(1,1,1,3,3,3-hexafluoropropan-2-yl)borate, tris(1,1,1,3,3,3-hexafluoro-2-phenyl-propan-2-yl)borate, tris(1,1,1,3,3,3-hexafluoro-2-(trifluoromethyl)propan-2-yl)borate, triphenyl borate, tris(4-fluorophenyl)borate, tris(2,4-difluorophenyl)borate, tris(2,3,5,6-tetrafluorophenyl)borate, tris(pentafluorophenyl)borate, tris(3-(trifluoromethyl)phenyl)borate, tris(3,5-bis(trifluoromethyl)phenyl)borate, tris(pentafluorophenyl)borane, or a mixture of any two or more thereof. Further suitable additives include 2-(2,4-difluorophenyl)-4-fluoro-1,3,2-benzodioxaborole, 2-(3-trifluoromethyl phenyl)-4-fluoro-1,3,2-benzodioxaborole, 2,5-bis(trifluoromethyl)phenyl-4-fluoro-1,3,2-benzodioxaborole, 2-(4-fluorophenyl)-tetrafluoro-1,3,2-benzodioxaborole, 2-(2,4-difluorophenyl)-tetrafluoro-1,3,2-benzodioxaborole, 2-(pentafluorophenyl)-tetrafluoro-1,3,2- benzodioxaborole, 2-(2-trifluoromethyl phenyl)-tetrafluoro-1,3,2-benzodioxaborole, 2,5-bis(trifluoromethyl phenyl)-tetrafluoro-1,3,2-benzodioxaborole, 2-phenyl-4,4,5,5-tetra(trifluoromethyl)-1,3,2-benzodioxaborolane, 2-(3,5-difluorophenyl-4,4,5,5-tetrakis(trifluoromethyl)-1,3,2-dioxaborolane, 2-(3,5-difluorophenyl-4,4,5,5-tetrakis(trifluoromethyl)-1,3,2-dioxaborolane, 2-pentafluorophenyl-4,4,5,5-tetrakis(trifluoromethyl)-1,3,2-dioxaborolane, bis(1,1,1,3,3,3-hexafluoroisopropyl)phenyl-boronate, bis(1,1,1,3,3,3-hexafluoroisopropyl)-3,5-difluorophenylboronate, bis(1,1,1,3,3,3-hexafluoroisopropyl)pentafluorophenylboronate, or a mixture of any two or more such compounds.

In some embodiments, each anion receptor is present at a concentration of about 0.001 to about 10 wt %.

Other additives may also be used in the electrolytes and electrochemical devices. For example, compounds such as, but not limited to, $Li_2B_{12}X_{12-n}H_n$, $Li_2B_{10}X_{10-n'}H_{n'}$, or a mixture of two or more of such compounds may be included in the electrolytes. In such compounds, X is OH, $OCH_3$, F, Cl, Br, or I, n is an integer from 0 to 12, and n' is an integer from 0 to 10. Such compounds may be present from about 0.001 to 15 wt %. In some embodiments, the compounds are present from about 0.001 to about 8 wt %.

In some embodiments, the electrode stabilizing additive is any of the above electrode stabilizing additives, or a mixture of any two or more such additives.

In some embodiments, the electrolyte is a gel electrolyte which includes the functional electrolyte solvent, at least one aprotic solvent; at least one lithium salt; at least one crosslinking agent; at least one monofunctional monomeric compound; and at least one radical reaction initiator. In some embodiments, the gel electrolyte may also include other electrode stabilization additives and other electrolyte additives.

In some embodiments, suitable crosslinking agents may be represented by Formula V:

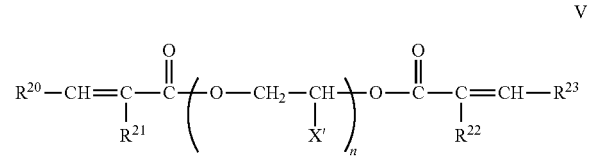

V where $R^{20}$, $R^{21}$, $R^{22}$, and $R^{23}$ are each independently H, an alkyl group having from 1 to 12 carbon atoms, or an alkenyl group having from 2 to 12 carbon atoms; and where X' is a hydrogen, methyl, or ethyl group, and n is an integer from 1 to 15. Monofunctional monomeric compounds may be used for the control of the crosslinking density of the gel electrolyte. Suitable monofunctional monomeric compounds include those of Formula VI:

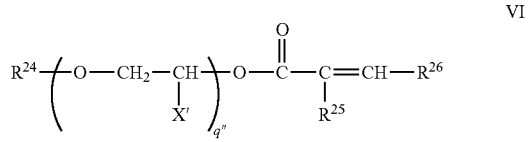

VI where $R^{24}$ is an alkyl group having from 1 to 12 carbon atoms; $R^{25}$ and $R^{26}$ are each independently H, an alkyl group having from 1 to 12 carbon atoms, or an alkenyl group having from 2 to 12 carbon atoms; X' is H, methyl or ethyl group; and q" is an integer from 1 to 20.

Crosslinking agents and monofunctional monomeric compounds provide a physical framework, or gel, after crosslinking to host the liquid phase. Variation of the amount of the crosslinking agent and monofunctional monomeric compound in the gel may impact the conductivity of the gel electrolyte due to changes in viscosity. Lower viscosity gels are prepared with higher concentrations of monofunctional monomeric compounds, as compared to the concentration of monofunctional monomeric compounds used for higher viscosity gels. Without being bound by theory, higher viscosity gels may be expected to have lower electrochemical conductivity, while lower viscosity gels may be expected to have higher electrochemical conductivity. However, other electrochemical properties of the gel electrolyte, or an electrochemical cell prepared with the gel electrolyte, such as oxidation potential and reduction potential, are not expected to be impacted.

Polymerization of crosslinking agents and monofunctional monomeric compounds are known to those of skill in the art. For example, monofunctional monomeric compounds may be polymerized by thermal and photoinitiation. Representative thermal initiators include, but are not limited to, an azo compound, a peroxide compound, bismaleimide, or a mixture of any two or more thereof. One example of an azo compound is azoisobutyronitrile. One example of a peroxide compound is benzoylperoxide. Representative photoinitiators include, but are not limited to, 1-hydroxyl-phenyl-ketone, benzophenone, 2-hydroxyl-2-methyl-1-phenyl-propanone, 2-hydroxyl-1-[4-(2-hydroxy)phenyl]-2-methyl-1-propanone, methylbenzoylformate, oxy-phenyl-acetic acid 2-[2-oxo-2-phenyl-acetoxy-ethoxy]-ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]-1-propanone, diphenyl(2,4,6-trimethylthio)phenyl)-phosphine oxide, phosphine oxide, phenyl bis(2,4,6-trimethyl benzoyl), bis($\eta^5$-2,4-cyclopentadien-1-yl)bis[2,6-difluoro-3-(1H-pyrrol-1-yl)phenyl]titanium, iodonium (4-methylphenyl)-[4-(2-methylpropyl)phenyl]-hexafluorophosphate, or a mixture of two or more thereof. In some instances, the photoinitiator is a UV initiator.

The present technology thus generally described will be understood more readily by reference to the following examples which are provided by way of illustration and are not intended to be limiting of the present technology.

EXAMPLES

Example 1

Synthesis of 1-methoxy-4-(2-methoxyethoxy)-2,5-di-tert-butyl-benzene. Scheme 1 is an illustration of the synthesis of the title compound.

Scheme 1:

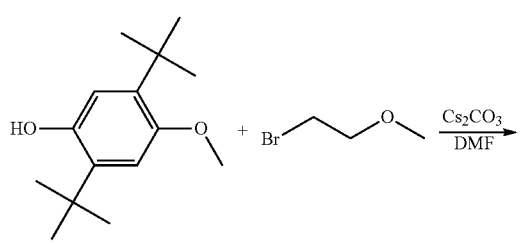

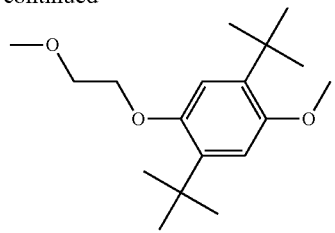

2,5-di-tert-butyl-4-methoxyphenol (9 mmol) was dissolved in anhydrous N,N-dimethylformamide (10 ml). Cesium carbonate (13 mmol) and 1-bromoethyl methyl ether (9 mmol) were added to the solution. The reaction mixture was then stirred at room temperature overnight. After removal of the solvent, the residue was partitioned between dichloromethane (DCM) and aqueous NaHCO$_3$ (0.1 M). The organic portion was separated and dried over Na$_2$SO$_4$ and then the solvent was removed under vacuum. The crude product was chromatographed (silica, hexanes/DCM from 5:1 to 1:1) to afford pure 1-methoxy-4-(2-methoxyethoxy)-2,5-di-tert-butyl-benzene in an 85% yield. $^1$H NMR (300 MHz, CDCl$_3$): δ/ppm 6.84 (s, 1H), 6.83 (s, 1H), 4.11 (t, J=4.5 Hz, 2H), 3.78 (m, 5H), 3.45 (s, 3H), 1.38 (s, 9H), and 1.35 (s, 9H).

Cyclic voltammograms were recorded for a solution of 0.01M 1-methoxy-4-(2-methoxyethoxy)-2,5-di-tert-butyl-benzene in an electrolyte of 1.2M LiPF$_6$ in EC/EMC (3:7 by weight) using a Pt/Li/Li three-electrode system (Pt working electrode, Li counter electrode and Li reference electrode) at various scan rates. See FIG. 1. One pair of reversible peaks is exhibited at about 3.8 to about 4.1 V vs. Li/Li$^+$. It is well known that the main electrolyte components (EC, PC, DMC, and LiPF$_6$) are electrochemically stable up to 4.8 V vs. Li/Li$^+$ or higher. The reversible electrochemical reaction at 3.8 V to 4.1 V vs. Li/Li$^+$ is therefore assigned to the reduction and oxidation peaks for the 1-methoxy-4-(2-methoxyethoxy)-2, 5-di-tert-butyl-benzene.

Figure 2:
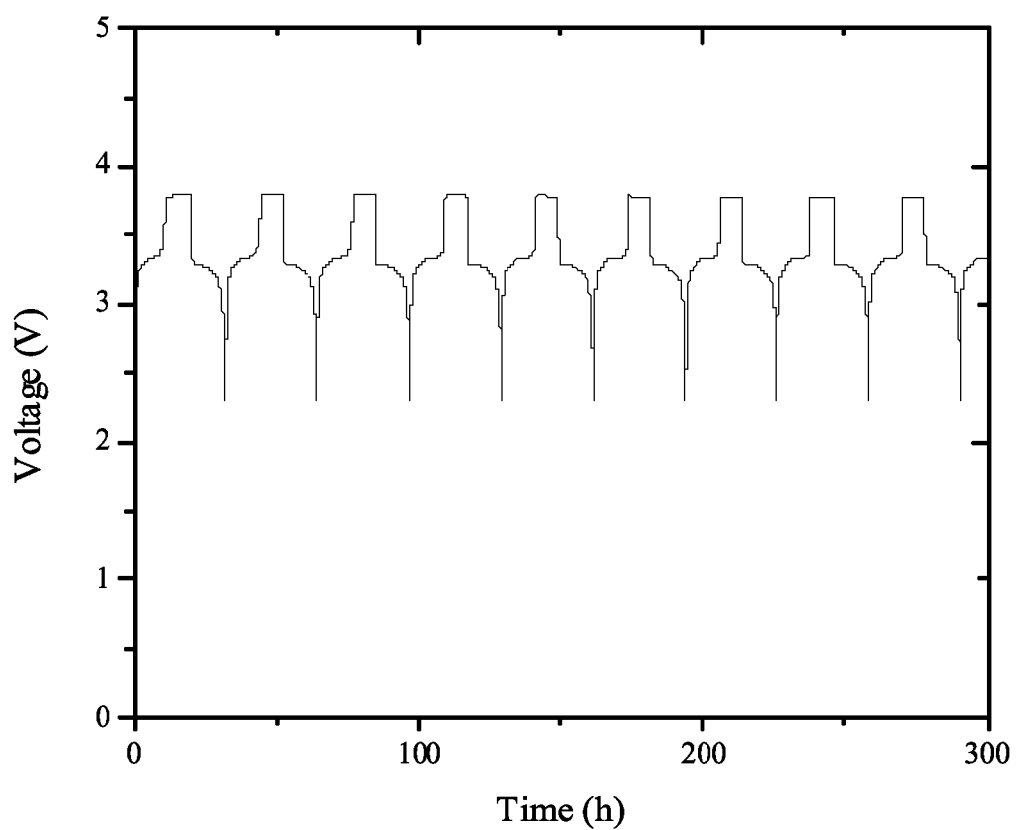
FIG. 2 is an overcharge test voltage profile of cells using MCMB and LFP as electrodes and containing 0.1 M 1-methoxy-4-(2-methoxyethoxy)-2,5-di-tert-butyl-benzene in 1.2M LiPF$_6$ in EC/EMC (3:7 by weight), charging rate is C/10 and overcharge 100%, according to Example 1.

Voltage profile overcharge test of cells using mesocarbon microbeads (MCMB) and LiFePO$_4$ (LFP) as electrodes, and containing 0.1 M 1-methoxy-4-(2-methoxyethoxy)-2,5-di-tert-butyl-benzene in the electrolyte of 1.2M LiPF$_6$ in EC/EMC (3:7 by weight) were recorded over the course of about 300 hours. See FIG. 2. The cells were charged at C/10 rate for 20 hours and then discharged to 2.2 V. The overcharge ratio ((charge capacity−discharge capacity)/discharge capacity) is 100%. For each cycle, after the capacity was fully charged, the cell voltage climbed quickly to 3.8 V, where the redox overcharge protection was activated, and then the voltage was constant for the following 10 hours until discharge. The flat plateau clearly indicates that the overcharge protection was effective, and extra electricity was shunted by the reversible redox behavior of the functional electrolyte.

Figure 3:
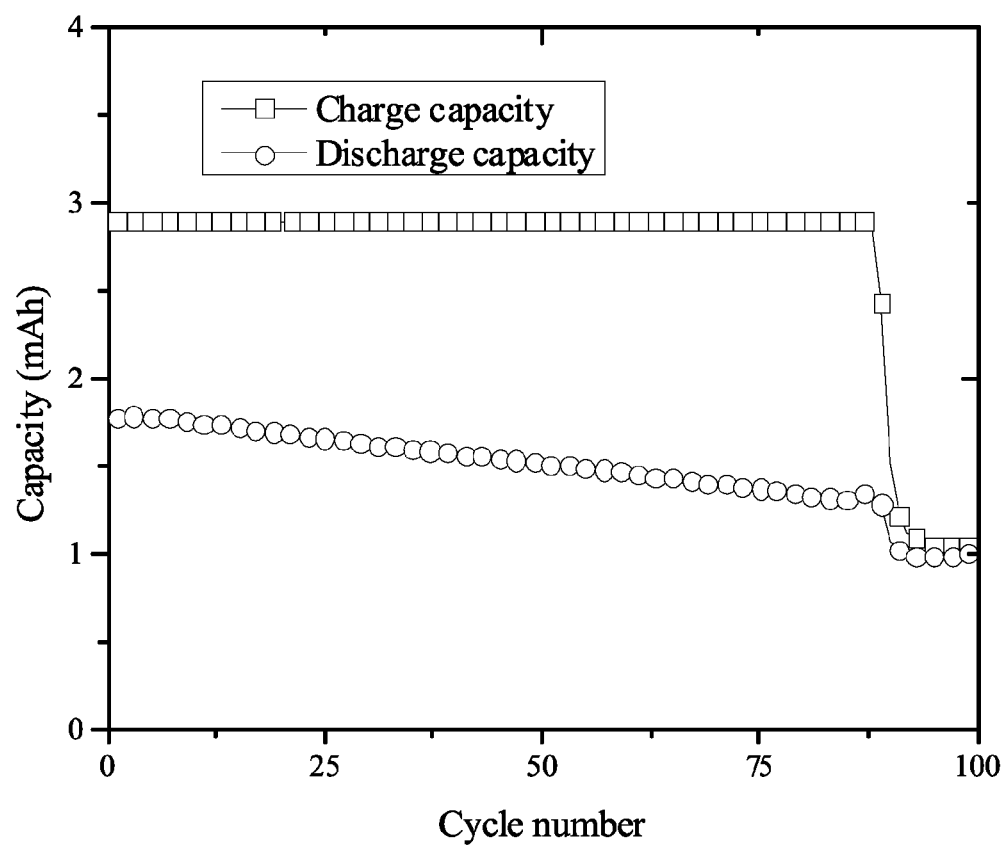
FIG. 3 is an overcharge test capacity profile of cells using MCMB and LFP as electrodes and containing 0.1 M 1-methoxy-4-(2-methoxyethoxy)-2,5-di-tert-butyl-benzene in the electrolyte of 1.2M LiPF$_6$ in EC/EMC (3:7 by weight), charging rate is C/10 and overcharge 100%, according to Example 1.

Capacity retention profiles of overcharge test of cells using MCMB and LFP as electrodes and containing 0.1M 1-methoxy-4-(2-methoxyethoxy)-2,5-di-tert-butyl-benzene in the electrolyte of 1.2M LiPF$_6$ in EC/EMC (3:7 by weight) were recorded. See FIG. 3. The charging rate was C/10, and the overcharge ratio was 100%. The difference between the charge and discharge capacity comes from the overcharge protection processes and equals the extra electricity carried by the functional electrolytes. After approximately 85 cycles, the shuttle appears to degrade.

Figure 4:
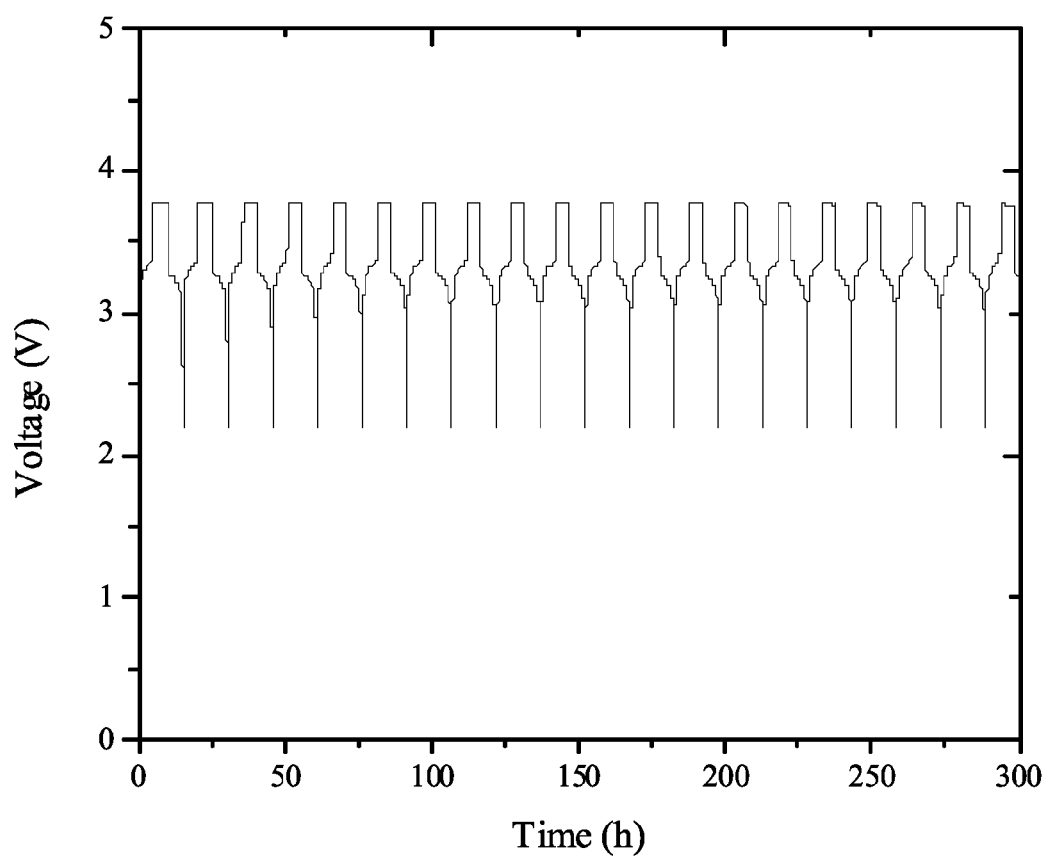
FIG. 4 is an overcharge test voltage profile of cells using MCMB and LFP as electrodes and containing 0.2 M 1-methoxy-4-(2-methoxyethoxy)-2,5-di-tert-butyl-benzene in the electrolyte of 1.2M LiPF$_6$ in EC/EMC (3:7 by weight), charging rate is C/5 and overcharge 100%, according to Example 1.

Voltage profile overcharge test of cells using mesocarbon microbeads MCMB and LFP as electrodes and containing 0.2 M 1-methoxy-4-(2-methoxyethoxy)-2,5-di-tert-butyl-benzene in an electrolyte of 1.2M LiPF$_6$ in EC/EMC (3:7 by weight) were recorded over the course of about 300 hours See FIG. 4. The charging rate was C/5, and the overcharge ratio was 100%. For each cycle, after the capacity was fully charged, the cell voltage climbed quickly to 3.8 V, where the redox overcharge protection was activated, and then the voltage stayed there for the next 10 hours until discharge. The flat plateau clearly indicates that the overcharge protection was effective, and extra electricity was shunted by the reversible redox behavior of the functional electrolyte.

Figure 5:
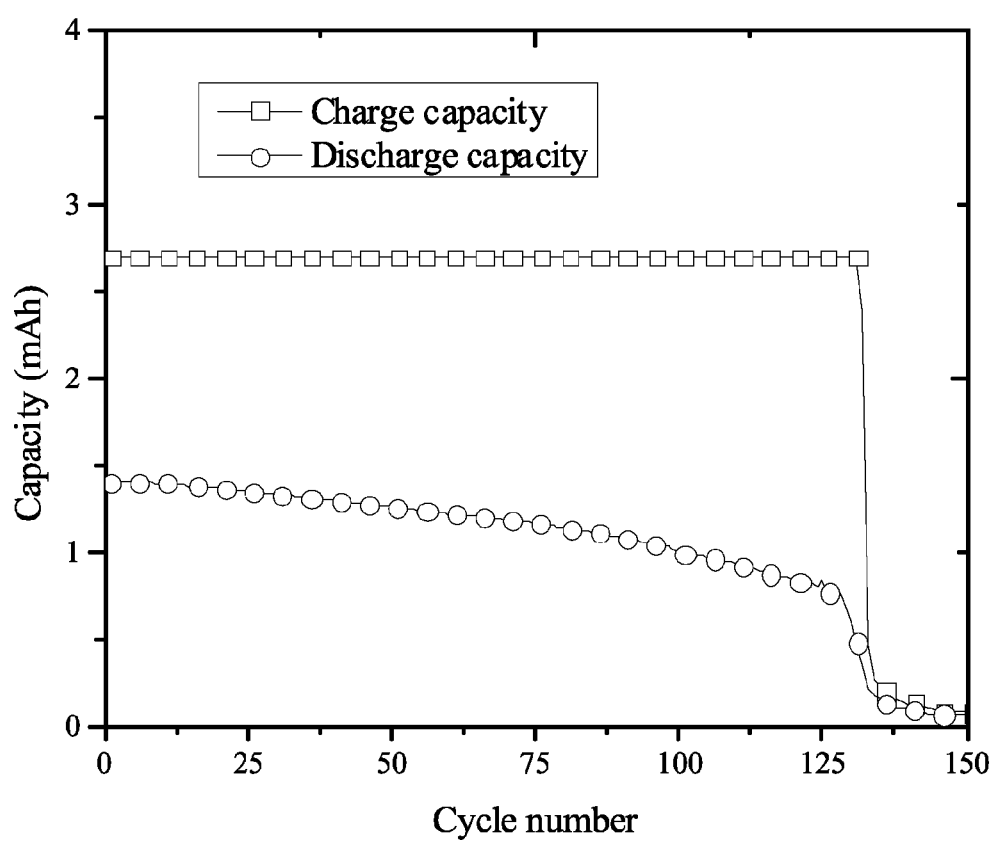
FIG. 5 illustrates capacity retention profiles of MCMB/LiFePO$_4$ cell containing 0.2 M 1-methoxy-4-(2-methoxyethoxy)-2,5-di-tert-butyl-benzene in the electrolyte of 1.2M LiPF$_6$ in EC/EMC (3:7 by weight) during the course of 0-3100 h. Charging rate is C/10 and overcharge is 100%, according to Example 1.

Capacity retention profiles of overcharge test of cells using MCMB and LFP as electrodes and containing 0.2M 1-(2-methoxyethoxy)methoxy-4-methoxy-2,5-di-tert-butyl-benzene were recorded. See FIG. 5. The charging rate was at C/10, and overcharge was 100%. The difference between the charge and discharge capacity comes from the overcharge protection processes and equals the extra electricity carried by the functional electrolytes. The electrolyte was observed to withstand more than 125 overcharge test cycles, exhibiting excellent overcharge protection.

Example 2

Synthesis of 1-methoxy-4-[2-(2-methoxyethoxy)ethoxy]-2,5-di-tert-butyl-benzene. Scheme 2 is an illustration of the synthesis of the title compound.

Scheme 2:

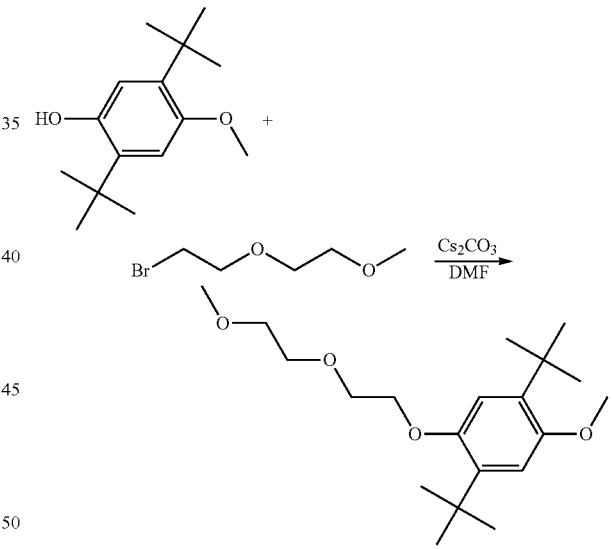

2,5-di-tert-butyl-4-methoxyphenol (9 mmol) was dissolved in anhydrous N,N-dimethylformamide (10 ml). Cesium carbonate (13 mmol) and 1-bromo-2-(2-methoxyethoxy)ethane (9 mmol) was added to the solution. The reaction mixture was then stirred at room temperature overnight. After removal of the solvent, the residue was partitioned between dichloromethane (DCM) and aqueous NaHCO$_3$ (0.1 M). The organic portion was separated and dried over Na$_2$SO$_4$ and then the solvent was removed under vacuum. The crude product was chromatographed (silica, hexanes/DCM from 5:1 to 1:1) to provide pure 1-methoxy-4-[2-(2-methoxyethoxy)ethoxy]-2,5-di-tert-butyl-benzene in an 87% yield. $^1$H NMR (300 MHz, CDCl$_3$): δ/ppm 6.83 (s, 1H), 6.82 (s, 1H), 4.14 (t, J=4.5 Hz, 2H), 3.89 (t, J=4.5 Hz, 2H), 3.80 (s, 3H), 3.72 (t, J=4.5 Hz, 2H), 3.58 (t, J=4.5 Hz, 2H), 3.40 (s, 3H), 1.38 (s, 9H)), and 1.35 (s, 9H). The purity was over 99.5% based GC-mass spectroscopy, and the molecular weight was observed at 338.3, which is consistent with the theoretical value, 338.5.

Figure 6:
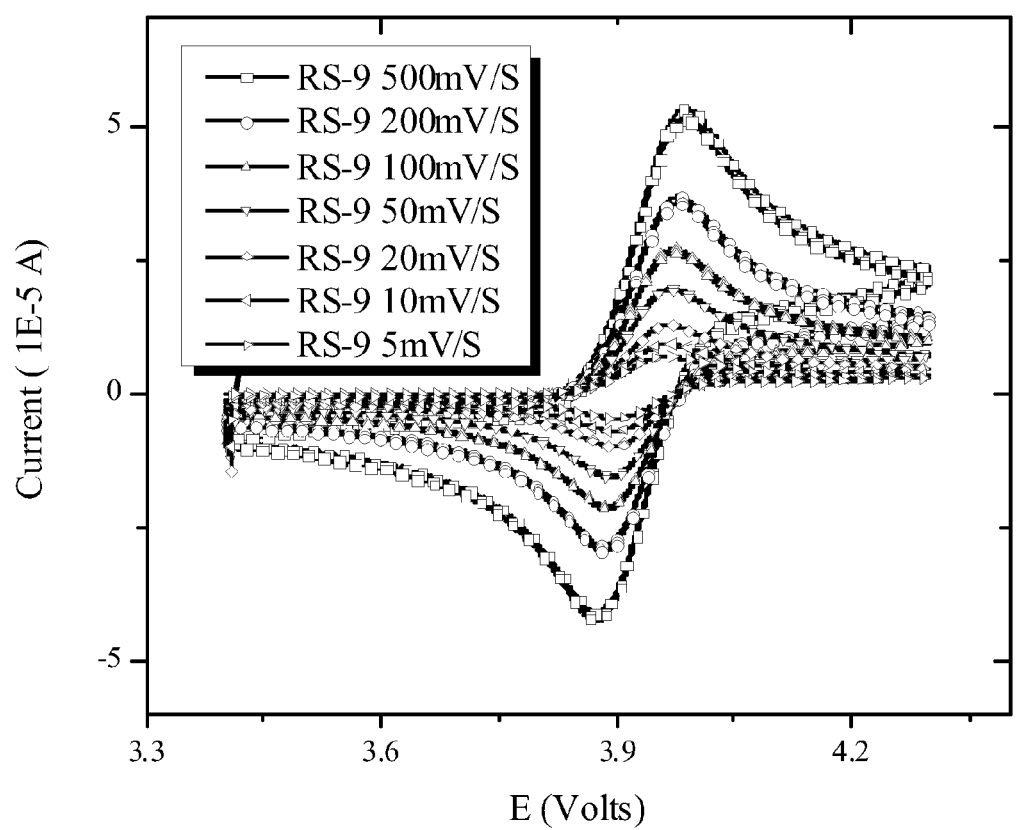
FIG. 6 illustrates a cyclic voltammogram of an electrolyte that includes 0.01 M 1-methoxy-4-[2-(2-methoxyethoxy)ethoxy]-2,5-di-tert-butyl-benzene in Gen 2 electrolyte at various rates using a Pt/Li/Li three-electrode system, according to Example 2.

Cyclic voltammograms were recorded for a solution of 0.01M 1-methoxy-4-[2-(2-methoxyethoxy)ethoxy]-2,5-di-tert-butyl-benzene in an electrolyte of 1.2M LiPF6 in EC/EMC (3:7 by weight), using a Pt/Li/Li three-electrode system at various scan rates. See FIG. 6. The reversible electrochemical reaction at 3.8-4.1 V vs. Li/Li$^+$is assigned to the redox reaction of the exemplary electrolyte solvent.

Figure 7:
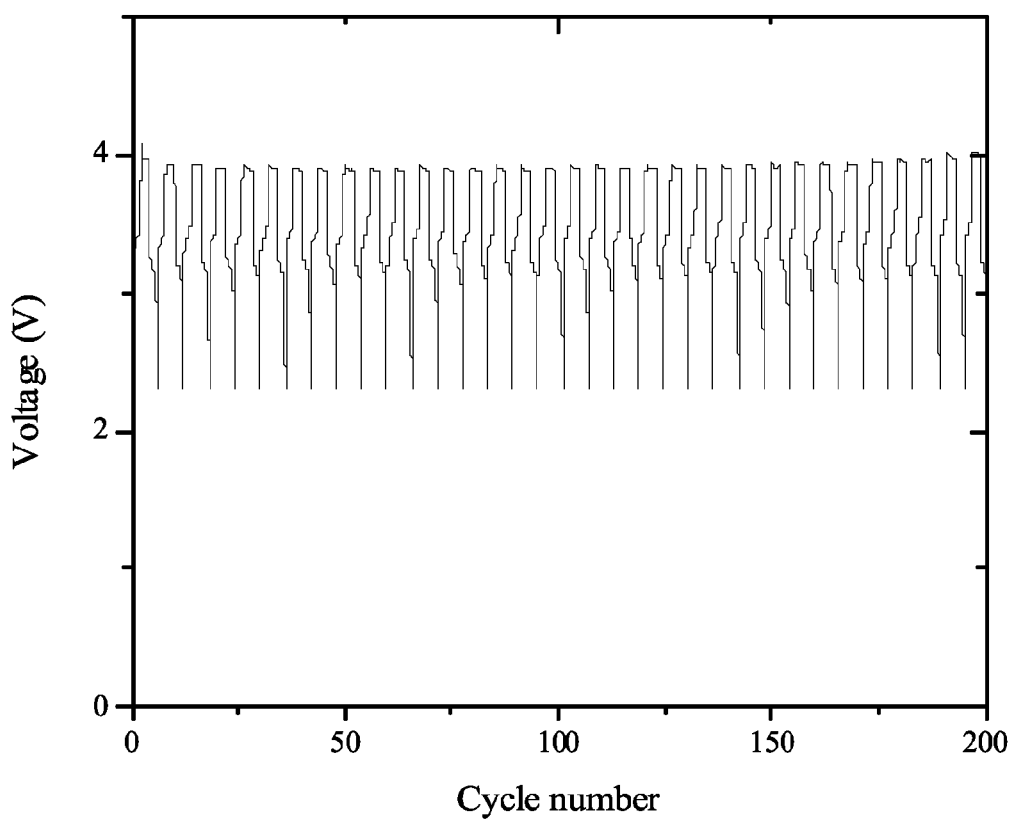
FIG. 7 is an overcharge test voltage profile of cells using MCMB and LFP as electrodes and containing 0.4 M 1-methoxy-4-[2-(2-methoxyethoxy)ethoxy]-2,5-di-tert-butyl-benzene, charging rate is C/2 and overcharge 100%, according to Example 2.

Voltage profiles overcharge test of a MCMB/LFP cell containing 0.4 M 1-methoxy-4-[2-(2-methoxyethoxy)ethoxy]-2,5-di-tert-butyl-benzene in 1.2M LiPF$_6$ in EC/EMC (3:7 by weight) were recorded over the course of 0-200 h. See FIG. 7. The charging rate was at C/2 and the overcharge was 100%. The electrolyte was observed to provide high rate overcharge protection at C/2 charging rate.

Figure 8:
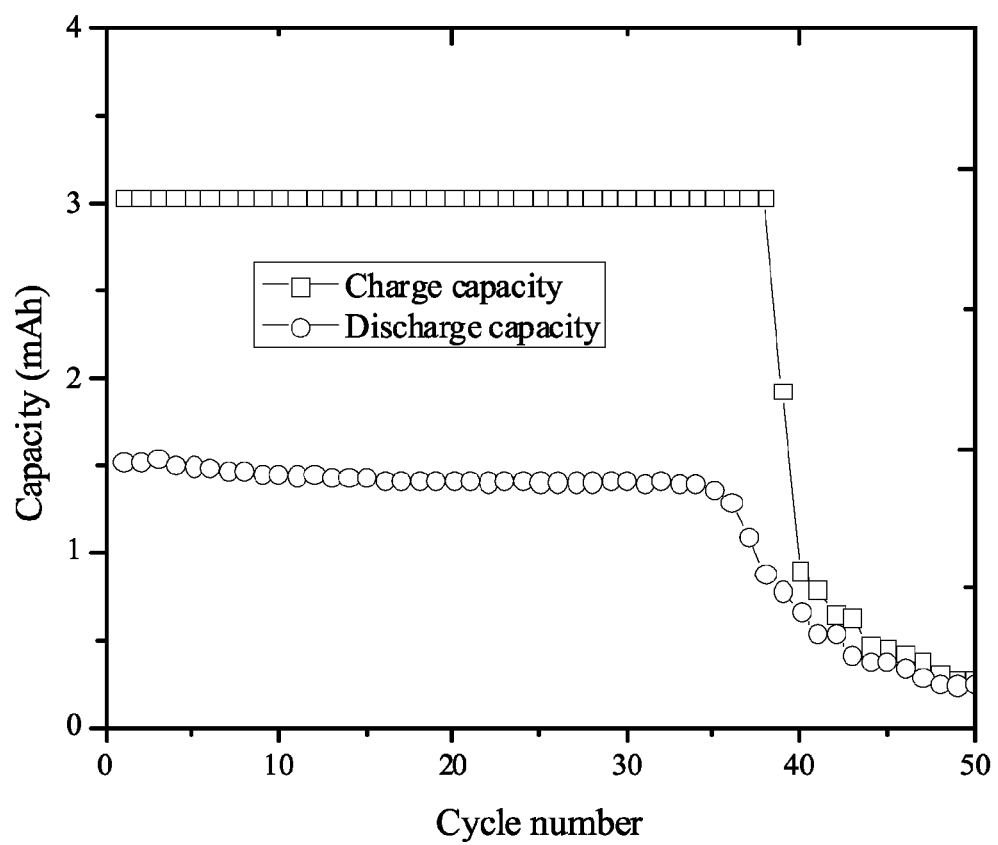
FIG. 8 is an overcharge test capacity profile of cells using MCMB and LFP as electrodes and containing 0.4 M 1-methoxy-4-[2-(2-methoxyethoxy)ethoxy]-2,5-di-tert-butyl-benzene, charging rate is C/2 and overcharge 100%, according to Example 2.

Capacity retention profiles of MCMB/LiFePO$_4$ cell containing 0.4 M 1-methoxy-4-[2-(2-methoxyethoxy)ethoxy]-2,5-di-tert-butyl-benzene in 1.2M LiPF$_6$ in EC/EMC (3:7 by weight) were recorded. See FIG. 8. The charging rate was at C/2 and the overcharge was 100%. Under these condition, the cells were observed to survive about 40 overcharge test cycles.

Figure 9:
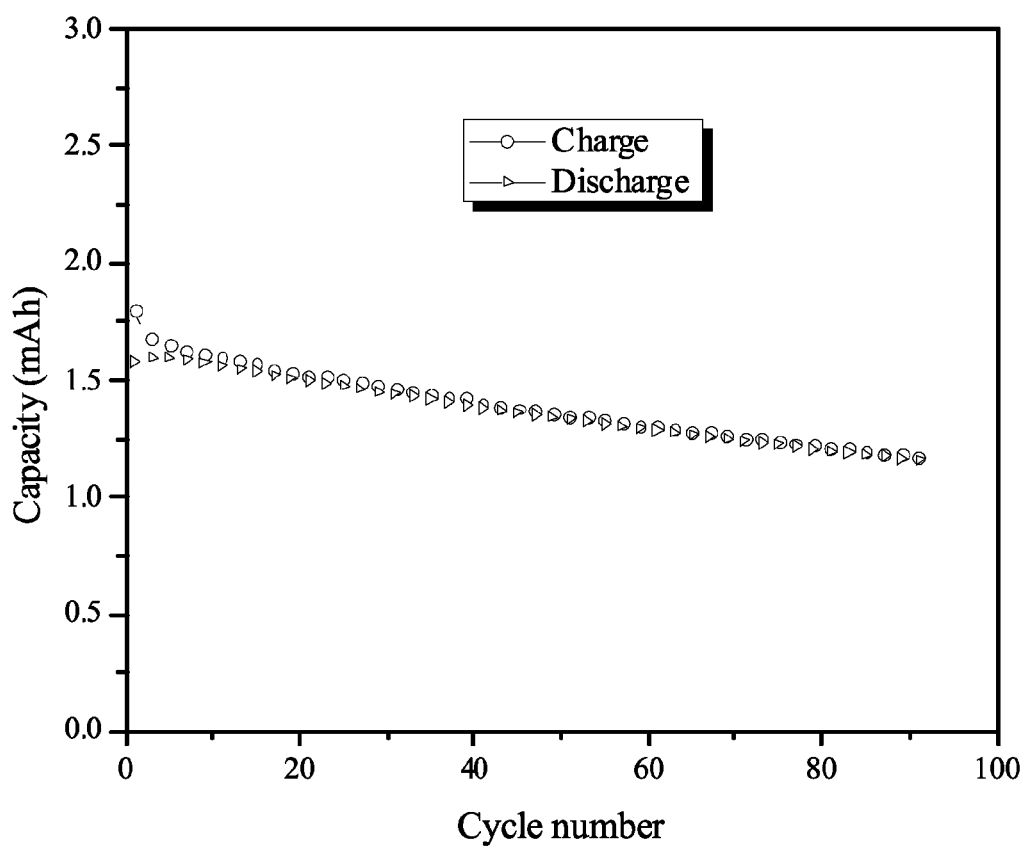
FIG. 9 illustrates capacity retention profiles of LFP/LTO cells using electrolyte of Gen 2: 1-methoxy-4-[2-(2-methoxyethoxy)ethoxy]-2,5-di-tert-butyl-benzene 2:1 by weight. The cells were cycled at room temperature from 1.5 V to 2.1 V at C/10 rate, according to Example 2.

Capacity retention profiles of LFP/LTO cells using an electrolyte of 2:1 [1,2M LiPF$_6$ in EC/EMC (3:7 by weight)] to [1-methoxy-4-[2-(2-methoxyethoxy)ethoxy]-2,5-di-tert-butyl-benzene] by weight were recorded. See FIG. 9. The cells were cycled at room temperature from 1.5 V to 2.1V at C/10 rate. Despite the degradation of the capacity, the cycle performance clearly indicated that 1-methoxy-4-[2-(2-methoxyethoxy)ethoxy]-2,5-di-tert-butyl-benzene can be used as co-solvent in the electrolyte system.

While certain embodiments have been illustrated and described, it should be understood that changes and modifications can be made therein in accordance with ordinary skill in the art without departing from the technology in its broader aspects as defined in the following claims.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:
1. A functional electrolyte solvent comprising a compound of formula

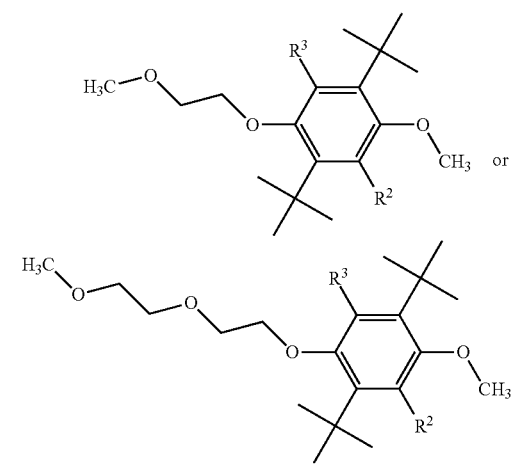

wherein:
R$^2$ is H, F, Cl, Br, I, alkyl, or a polyether group; and
R$^3$ is H, F, Cl, Br, I, alkyl, or a polyether group.
2. The functional electrolyte solvent of claim 1, wherein the compound has the structure

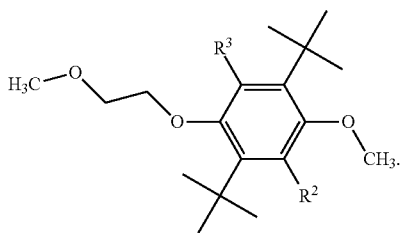

3. The functional electrolyte solvent of claim 1, wherein the compound has the structure:

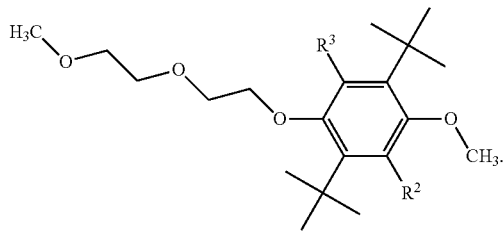

4. The functional electrolyte solvent of claim 1, wherein the compound is:

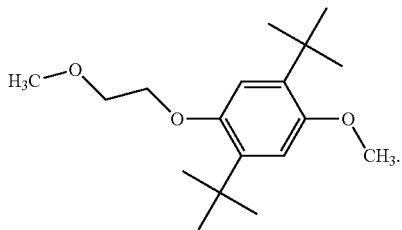 [SMILES: COCCOc1cc(C(C)(C)C)c(OC)cc1C(C)(C)C]

5. The functional electrolyte solvent of claim 1, wherein the compound is:

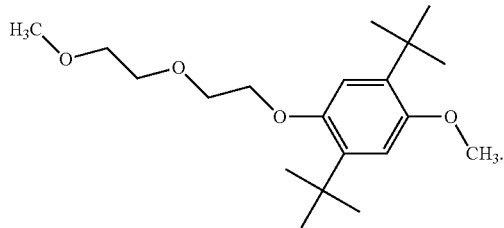 [SMILES: COCCOCCOc1cc(C(C)(C)C)c(OC)cc1C(C)(C)C]

6. An electrolyte comprising:
the functional electrolyte solvent of claim 1; and
an alkali metal salt.

7. The electrolyte of claim 6, wherein the functional electrolyte solvent is a redox active material and has a redox potential of 3 to 5 V.

8. The electrolyte if claim 6, wherein the functional electrolyte solvent is 1-methoxy-4-(2-methoxyethoxy)-2,5-di-tert-butyl-benzene, 1-methoxy-4-[2-(2-methoxyethoxy)ethoxy]-2,5-di-tert-butyl-benzene, or a mixture thereof.

9. The electrolyte of claim 6, wherein the concentration of the functional electrolyte solvent in the electrolyte is from 0.0005 wt % and 60 wt %.

10. The electrolyte of claim 6, wherein the alkali metal salt is a lithium salt.

11. The electrolyte of claim 6, wherein the alkali metal salt is Li[(C$_2$O$_4$)$_2$B], Li(C$_2$O$_4$)BF$_2$, LiClO$_4$, LiBF$_4$, LiAsF$_6$, LiPF$_6$, LiCF$_3$SO$_3$, Li(CF$_3$SO$_2$)2N, Li(CF$_3$SO$_2$)$_3$C, LiN(SO$_2$C$_2$F$_5$)$_2$, lithium alkyl fluorophosphates, or a mixture of any two or more thereof.

12. The electrolyte of claim 6 further comprising a polar aprotic solvent.

13. The electrolyte of claim 12, wherein the polar aprotic solvent is selected from ethylene carbonate, propylene carbonate, dimethyl carbonate, diethyl carbonate, ethyl methyl carbonate, dimethyl ether, gamma butyrolactone, or a mixture of any two or more thereof.

14. The electrolyte of claim 6, wherein the alkali metal salt is other than Li[(C$_2$O$_4$)$_2$B], Li(C$_2$O$_4$)BF$_2$, and the electrolyte further comprises about 0.001 wt % to about 8 wt % of an electrode stabilizing additive that is Li[(C$_2$O$_4$)$_2$B], Li(C$_2$O$_4$)BF$_2$, or a mixture thereof.

15. The electrolyte of claim 6 further comprising an electrode stabilizing additive that is a substituted or unsubstituted spirocyclic hydrocarbon containing at least one oxygen atom and at least one alkenyl or alkynyl group.

16. An electrochemical device comprising:
a cathode
an anode; and
an electrolyte of claim 6.

17. The electrochemical device of claim 16, wherein the device is a lithium secondary battery; the cathode is a lithium metal oxide cathode; the anode is a carbon or lithium metal anode; and the anode and cathode are separated from each other by a porous separator.

18. An electrolyte comprising:
an alkali metal salt; and
at least one of 1-methoxy-4-(2-methoxyethoxy)-2,5-di-tert-butyl-benzene, 1-methoxy-4-[2-(2-methoxyethoxy1)ethoxy]-2,5-di-tert-butyl-benzene, 1-methoxy-4-[2-[2-(2-ethoxyethoxyl)ethoxy]ethoxy]-2,5-di-tert-butyl-benzene, 1-methoxy-4-[2-[2-[2-(2-methoxyethoxyl)ethoxy]ethoxy]ethoxy]-2,5-di-tert-butyl-benzene, 1-methoxy-4-[2-[2-[2-[2-(2-methoxyethoxyl)ethoxy]ethoxy]ethoxy]ethoxy]-2,5-di-tert-butyl-benzene, and 1-methoxy-4-[2-[2-[2-[2-[2-(2-methoxyethoxyl)ethoxy]ethoxy]ethoxy]ethoxy] ethoxyl-2,5-di-tert-butyl-benzene.

* * * * *

UNITED STATES PATENT AND TRADEMARK OFFICE
CERTIFICATE OF CORRECTION

PATENT NO. : 9,005,822 B2  
APPLICATION NO. : 13/787433  
DATED : April 14, 2015  
INVENTOR(S) : Lu Zhang, Zhengcheng Zhang and Khalil Amine Page 1 of 1

It is certified that error appears in the above-identified patent and that said Letters Patent is hereby corrected as shown below:

In the Claims

In Column 24, Claim 8, Line 6, remove "(2-methoxyethoxyl)" and replace with --(2-methoxyethoxy)--.

In Column 24, Claim 11, Line 15, remove "Li($CF_3SO_2$)2N," and replace with --Li($CF_3SO_2$)$_2$N,--.

In Column 24, Claim 18, Lines 46 and 47, remove "(2-methoxyethoxyl)" and replace with --(2-methoxyethoxy)--.

In Column 24, Claim 18, Line 48, remove "(2-ethoxyethoxyl)" and replace with --(2-ethoxyethoxy)--.

In Column 24, Claim 18, Line 50, remove "methoxyethoxyl)" and replace with --methoxyethoxy)--.

In Column 24, Claim 18, Line 52, remove "methoxyethoxyl)" and replace with --methoxyethoxy)--.

In Column 24, Claim 18, Line 54, remove "(2-methoxyethoxyl)" and replace with --(2-methoxyethoxy)--.

Signed and Sealed this  
Eighteenth Day of August, 2015

Michelle K. Lee  
*Director of the United States Patent and Trademark Office*